US010369408B2

(12) United States Patent
Keller et al.

(10) Patent No.: US 10,369,408 B2
(45) Date of Patent: Aug. 6, 2019

(54) AIR RESISTANCE DEVICE

(71) Applicant: Halcyon Research, Inc., Sarasota, FL (US)

(72) Inventors: Dana Kesslen Keller, Sarasota, FL (US); Mary Lou Casadevall-Keller, Sarasota, FL (US)

(73) Assignee: HALCYON RESEARCH, INC., Sarasota, FL (US)

( * ) Notice: Subject to any disclaimer, the term of this patent is extended or adjusted under 35 U.S.C. 154(b) by 180 days.

(21) Appl. No.: 15/466,923

(22) Filed: Mar. 23, 2017

(65) Prior Publication Data

US 2017/0189749 A1 Jul. 6, 2017

Related U.S. Application Data

(63) Continuation-in-part of application No. 14/409,883, filed as application No. PCT/US2014/046641 on Jul. 15, 2014, now abandoned.

(60) Provisional application No. 62/311,968, filed on Mar. 23, 2016, provisional application No. 61/856,283, filed on Jul. 19, 2013.

(51) Int. Cl.
| | |
|---|---|
| *G10D 7/12* | (2006.01) |
| *A61M 16/00* | (2006.01) |
| *A61M 16/08* | (2006.01) |
| *A63B 21/00* | (2006.01) |
| *A63B 21/02* | (2006.01) |
| *A63B 21/06* | (2006.01) |
| *A63B 23/18* | (2006.01) |
| *A63B 21/008* | (2006.01) |

(52) U.S. Cl.
CPC ......... *A63B 23/18* (2013.01); *A61M 16/0006* (2014.02); *A63B 21/0004* (2013.01); *G10D 7/123* (2013.01); *A61M 16/0866* (2014.02); *A61M 2205/0205* (2013.01); *A61M 2205/43* (2013.01); *A61M 2205/44* (2013.01); *A63B 21/0085* (2013.01); *A63B 21/027* (2013.01); *A63B 21/06* (2013.01)

(58) Field of Classification Search
CPC ....... A63B 23/18; A63B 21/00; A63B 21/008; A63B 21/0085; A63B 21/0088; A63B 23/185; G10D 7/123; A61M 16/0006; A61M 2205/43; A61M 2205/0205; A61M 2205/44; A61M 16/0866
USPC .............................. 482/13, 92, 111–113, 148
See application file for complete search history.

(56) References Cited

U.S. PATENT DOCUMENTS

| | | | |
|---|---|---|---|
| 364,610 A | 6/1887 | Stratton | |
| 3,674,910 A * | 7/1972 | McKenzie | ............. G10D 7/123 84/377 |
| 4,196,650 A * | 4/1980 | Fricke | .................. G10H 1/0558 84/687 |

(Continued)

OTHER PUBLICATIONS

International Search Report and Written Opinion of corresponding International Application No. PCT/US201/046641 dated Nov. 24, 2014; 7 pages.

*Primary Examiner* — Garrett K Atkinson
(74) *Attorney, Agent, or Firm* — Shumaker, Loop & Kendrick, LLP

(57) ABSTRACT

An attachment for a harmonica or a pulmonary harmonica may include a resistance band or modified comb which increases respiratory resistance from the typical open holes of harmonicas. The resistance band or modified comb may prevent a broken reed from being inhaled into the mouth.

15 Claims, 15 Drawing Sheets

(56) References Cited

U.S. PATENT DOCUMENTS

| | | | | |
|---|---|---|---|---|
| 5,042,467 A | * | 8/1991 | Foley | A61M 15/0086 128/200.14 |
| 5,899,832 A | * | 5/1999 | Hougen | A63B 23/18 128/200.24 |
| 6,058,932 A | * | 5/2000 | Hughes | A61H 23/0236 128/200.24 |
| 6,083,141 A | * | 7/2000 | Hougen | A61M 16/0006 128/202.16 |
| 6,176,235 B1 | * | 1/2001 | Benarrouch | A61F 11/00 128/200.24 |
| 6,326,532 B1 | * | 12/2001 | Antaki | G10D 7/123 84/377 |
| 6,702,769 B1 | * | 3/2004 | Fowler-Hawkins | A61H 23/0236 128/200.24 |
| 6,845,270 B2 | | 1/2005 | Debrouse | |
| 6,984,214 B2 | * | 1/2006 | Fowler-Hawkins | A61H 23/0236 128/200.24 |
| 8,563,346 B2 | | 10/2013 | Song et al. | |
| 8,653,346 B2 | * | 2/2014 | Schaman | G10D 7/123 84/377 |
| 2004/0158178 A1 | * | 8/2004 | Fowler-Hawkins | A61H 23/0236 601/46 |
| 2006/0223675 A1 | * | 10/2006 | Lew | A63B 23/18 482/13 |
| 2013/0036893 A1 | * | 2/2013 | Schaman | G10D 7/123 84/377 |
| 2018/0330702 A1 | * | 11/2018 | Schille | G10H 1/386 |

\* cited by examiner

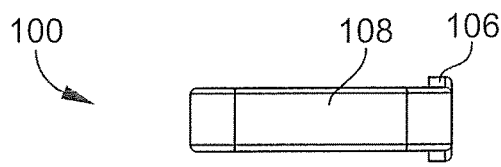
Fig. 18A
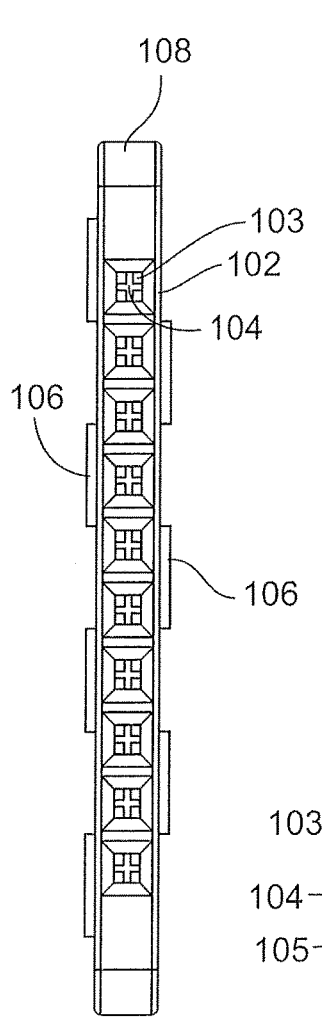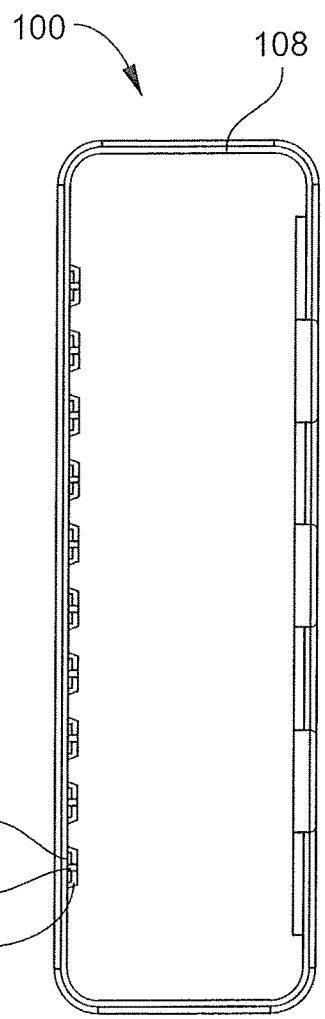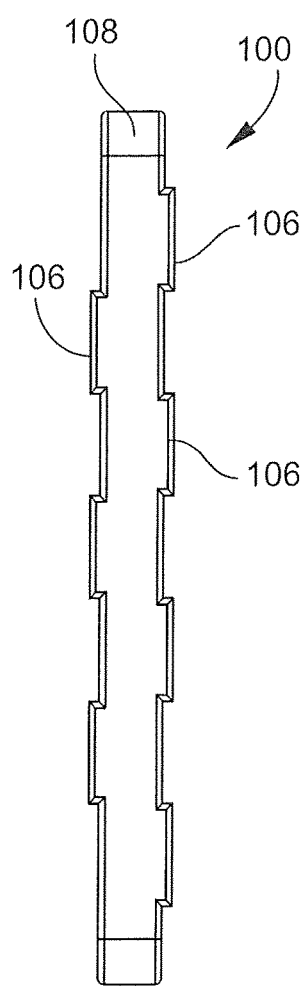
Fig. 18B  Fig. 18C  Fig. 18D
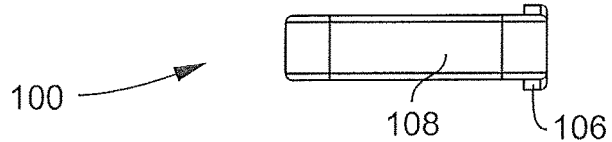
Fig. 18E

AIR RESISTANCE DEVICE

CROSS REFERENCE TO RELATED APPLICATIONS

This application is non-provisional claiming priority to U.S. Provisional Application No. 62/311,968, filed on Mar. 28, 2016. This application is also a Continuation-in-Part of U.S. National Stage application Ser. No. 14/409,883, filed on Dec. 19, 2014 which claims priority to PCT International Application No. PCT/US2014/046641, filed Jul. 15, 2014, which claims priority to U.S. Provisional Application No. 61/856,283 filed Jul. 19, 2013; the entire contents of each are expressly incorporated herein by reference.

TECHNICAL FIELD AND BACKGROUND OF THE INVENTION

The present invention relates generally to the field of pulmonary instruments and, more particularly, to the field of devices and methods for the treatment of and prevention of pulmonary illnesses and diseases. The present invention is a breathing resistance device which may be attached to a harmonica or built into a harmonica, such as a pulmonary, harmonica to aid in treatment of certain lung and breathing conditions.

Pulmonary illnesses and diseases impact people around the world. By the time we are in our thirties, we begin losing lung capacity and by middle age, the capacity is decreased by fifty percent. It will be appreciated by those of ordinary skill in the art that such illnesses include asthma, bronchitis, emphysema, chronic obstructive pulmonary disease (COPD), and other bronchial, sinus, and airflow obstructing diseases. Such conditions may result from smoking, occupational exposures, air pollution, genetics, autoimmune diseases, acute exacerbations, and the like. People with such impaired lung function often have tenacious secretions that they cannot cough up and that worsen their condition. Additionally, many people, especially those overweight, have become habitual shallow breathers, which deprives them of sufficient oxygen for optimum health.

People do not enjoy using standard respiratory therapy devices because they are boring and clearly medical devices.

Traditional treatments have focused oral and intravenous medications as well as nebulizer and spacer administered medications. Despite the availability of such treatments for the conditions, respiratory muscle dysfunction frequently persists and worsens in patients.

Because of the muscle dysfunction, pulmonary patients are often referred to additional treatment in the form of pulmonary rehabilitation. Inspiratory and expiratory muscle training has sometimes been used instead of or in addition to such pulmonary rehabilitation. Such inspiratory muscle training has been recommended to be performed using a pressure or resistance device for a duration and frequency of up to 15-30 minutes and as often as 5-7 days per week. However, people do not enjoy using standard respiratory therapy devices because the devices are boring and clearly medical devices reminiscent of hospitals and the like. The monotony and relative frequency associated with such treatments may result in diminished effectiveness of treatments as patients may apply the treatments less often than recommended and for shorter durations than recommended. Likewise, patients may simply discontinue the treatments, being non-compliant with recommended self-care. Therefore, there is a need in the art for an effective pulmonary rehabilitation treatment using inspiratory and expiratory muscle training that improves the negative effects of muscle dysfunction and also encourages treatment regimen retention. There is also a need in the art for an effective pulmonary rehabilitation treatment using inspiratory and expiratory muscle training that loosens tenacious lung secretions and other fluids which can then be coughed up or otherwise eliminated from the body. There is also a need in the art for an effective pulmonary rehabilitation treatment using inspiratory and expiratory muscle training that promotes deep, abdominal breathing (i.e., diaphragmatic breathing). There is also a need in the art for an effective pulmonary rehabilitation treatment using inspiratory and expiratory muscle training that encourages continued use of the treatment device so that use of the device and the benefits of increased abdominal breathing both become habitual through practice. There is also a need in the art for an effective pulmonary rehabilitation treatment using inspiratory and expiratory muscle training that is smooth, attractive and pleasant to use, which empowers patients, although one with sharper edges would still be functional.

Further, standard harmonicas provide minimal resistance against breathing, so there is little exercise for the muscles that power the lungs. There is also the possibility of a harmonica reed breaking and entering the user's respiratory or digestive systems if inhaled or swallowed. There is a still further need in the art for a device which may be attached to or built into existing harmonicas, and/or to pulmonary harmonicas, to further aid in rehabilitation treatment. There is also a need in the art for a device which protects the user from inhalation or ingestion of bits of harmonica reeds which may break during use.

SUMMARY OF THE INVENTION

It is therefore an object of the present invention to provide an effective pulmonary rehabilitation treatment using inspiratory and expiratory muscle training that improves the negative effects of muscle dysfunction and also encourages treatment regimen retention.

It is a further object of the present invention to provide an effective pulmonary rehabilitation treatment using inspiratory and expiratory muscle training that loosens lung secretions and other fluids that can then be more easily eliminated.

It is a further object of the present invention to provide an effective pulmonary rehabilitation treatment using inspiratory and expiratory muscle training that promotes long, slow, deep, and complete abdominal breathing.

It is a further object of the present invention to provide an effective pulmonary rehabilitation treatment using inspiratory and expiratory muscle training that encourages continued use of the treatment device so that use of the device and developed abdominal breathing both become habitual through practice.

It is a further object of the present invention to provide an effective pulmonary rehabilitation treatment using inspiratory and expiratory muscle training that is smooth, attractive and pleasant to use, which empowers patients, although such a device with sharper edges would be effective but not the optimal presentation of the device.

It is a further object of the invention to provide an effective pulmonary rehabilitation treatment using inspiratory and expiratory muscle training which treatment may utilize a resistance band attachment for a harmonica or a pulmonary harmonica, as described herein.

It is a further object of the invention to provide a resistance band attachment or built in device for a harmonica or a pulmonary harmonica, as described herein, which prevents harmonica or pulmonary harmonica reeds from entering a user's mouth in the event they break during use.

Further objects of the invention include helping people with respiratory disorders such as chronic obstructive pulmonary disease (COPD), asthma, chest or sinus congestion, or people with the desire for pulmonary therapy, to breathe better and enjoy life more. The invention, when used with a harmonica or pulmonary harmonica, is particularly designed to promote diaphragmatic breathing and produce deep, resonant, meditative sound waves that can be felt in the users' lungs but also penetrate to the sinuses. Used in this way, the invention requires no musical talent or ability whatsoever, and no prior experience with controlled breathing or meditative exercises and techniques. Used in this way, the invention is specifically designed to be smooth and comfortable to hold, with smooth edges that will prevent nicks and cuts in users with compromised immune systems or thinned skin in its optimal presentation.

The presently disclosed invention may be utilized in or in conjunction with a pulmonary harmonica and method for using a pulmonary harmonica device. The harmonica has low frequency notes that deliver powerful vibrations (pulses) to the user's respiratory system. When the resistance device and method are used with a harmonica, as users blow and draw breaths through the low notes on this pulmonary harmonica, harmonic vibrations pulse the lungs and help loosen secretions that can be coughed up. The resistance device of the present invention adds further resistance to air flow through the harmonica and promotes long, slow, deep, complete, abdominal breathing, which is continued after use because it becomes habitual through practice.

According to one embodiment of the invention, the resistance device is attached to or built into a pulmonary harmonica for promoting deep abdominal breathing by a user having an outer housing, a comb having a mouthpiece portion and one or more holes, one or more reed plates, a plurality of reeds, located on the reed plates (unless the comb is designed to include that function), tuned to vibrate at low frequencies and to emit low frequency sound waves producing a harmonic resonance when blown or drawn by a user, which pulses in the user's respiratory system resulting in the break-up of mucus, and fastening hardware for securing the comb, securing reeds to the reed plate (unless glued, melded, welded, brazed, or soldered) and the reed plate to the outer housing. In its extreme, the entire instrument could be molded or otherwise fashioned from fewer individual pieces, culminating in a single piece of material appropriately designed to deliver the same type of pulsing to the lungs from breathing through reeds.

According to another embodiment of the invention, the pulmonary harmonica may include that each one of the reeds is heavy, relative to reeds of a traditional harmonica in the same position (or hole) on the harmonica. This extra weight provides a variable resistance across several holes that helps build respiratory strength.

According to another embodiment of the invention, the pulmonary harmonica's lowest tuned reed has a frequency no higher than 150 Hz.

According to another embodiment of the invention, the pulmonary harmonica can be tuned to different tonal scales, such as having one or more reeds tuned to a frequency of 136.1 Hz or other chakra frequency below 150 Hz.

According to another embodiment of the invention, the comb may have 10 holes and the reeds may be further tuned to full diatonic scales of chords in a major or minor key.

According to another embodiment of the invention, the comb may include a single and only a single hole, the one or more reed plates may include a single and only a single reed plate, and the plurality of reeds may include two and only two reeds.

According to another embodiment of the invention, the outer housing may include two smooth cover plates.

According to another embodiment of the invention, the smooth cover plates, comb, and the reeds further may include anti-microbial materials for improved hygienic function.

According to another embodiment of the invention, the fastening hardware may be selected from the group comprising screws, bolts, rivets, nails, welds, melds, and glues.

According to another embodiment of the invention, the pulmonary harmonica may include a built-in force guide which elicits a buzzing sound from one of the reeds when the device is used with excessive force during inhalation by the user.

According to another embodiment of the invention, the pulmonary harmonica may include a built-in force guide which elicits a buzzing sound from one of the reeds when the device is used with excessive force during exhalation by the user.

According to another embodiment of the invention, the device may be tuned in order to provide a pleasant sound in its optimal presentation. The device is smooth, attractive and pleasant to use, which empowers patients. The present invention may be characterized by lack of a discordant sound which is present and heard in traditionally tuned harmonicas. Thus, the present invention is even more suitable for people with no musical ability. Use of the harmonica device of the present invention may motivate patients to continue to use the treatment. The device may provide strong vibrations to the lungs.

Rather than having sharp edges that can cut fragile skin, the optimal presentation of the harmonica, as used with the resistance device, has an exterior surface that is smooth, although some presentations of the harmonica could have sharp edges and still develop effective low frequency pulses. The optimal presentation of the harmonica may be considered attractive and pleasant to use.

According to an aspect of the invention, the harmonica used with the resistance device may include a comb, reeds, some of which may have weights on the end, reed plate(s), cover plate(s), and fastening hardware such as screws.

According to another aspect of the invention, the harmonica used with the resistance device may include two cover plates—upper and lower, two reed plates with reeds attached, and a central comb with holes for mouthpiece and air movement, and fasteners to attach the reeds to the reed plates and secure all components together.

According to another aspect of the invention, the harmonica used with the resistance device may include as few as one sounding hole and one reed plate, as long as there are at least two reeds tuned to resonant frequencies, and could be square, rectangular, cylindrical, curved or other overall shape in appearance.

According to another aspect of the invention, the harmonica used with the resistance device may include any number of sounding holes. Ten holes allows for two full diatonic scales, including scales of chords in key, which may provide a wide range of resistance training and may be tuned to allow the user to play songs.

According to another aspect of the invention, the harmonica used with the resistance device may include a number of screws used to fasten the reed plates to the comb.

The harmonica parts may be fastened from a single side using tapped holes on the opposing reed plate for fastening or parts could be nailed, welded, glued, or otherwise fastened together.

According to another aspect of the invention, the harmonica used with the resistance device may be tuned to different frequencies. According to one such aspect, some reeds may be tuned to a specific frequency that is not a standard musical note, such as 136.1 Hz, which is commonly acknowledged to be the frequency of the mystical Sanskrit symbol OM and the Hindu heart Chakra. This aspect of the invention specifically contemplates tuning the reeds to various Chakra frequencies. In tuning the harmonica in this way, the harmonica will make a sound that can be highly meditative or evocative to followers of Hinduism, Buddhism, Sikhism, and Jainism, as well as to people who meditate without a specific affiliation.

According to another aspect of the invention, the harmonica used with the device may include an upper limit on the lowest frequency reed for the invention of 150 Hz. Further, optimal pulsing can be achieved for most people by using a range of single reed frequencies below 150 Hz as the lower notes and combining them as chords. Using multiple reeds below 150 Hz further optimizes the usefulness of the invention for more people by offering a user-selectable amount of pulsing for their lungs. For convenience, the pulsing effect can be generated by the invention when reduced to as few as one hole and two reeds tuned to resonant frequencies.

According to another aspect of the invention, the harmonica used with the device may include the cover plates configured with a relatively low profile. Such a configuration may include a built-in force guide which elicits a buzzing of one of the reeds when the device is used with excessive force during inhalation on low chords.

According to another aspect of the invention, the harmonica used with the device may include the cover plates configured with a relatively low profile. Such a configuration may include a built-in force guide which elicits a buzzing of one of the reeds when the device is used with excessive force during exhalation on low chords.

According to another aspect of the invention, the harmonica used with the device may encourage longer reed life by limiting the travel of the lower pitched reeds.

According to another aspect of the invention, the harmonica used with the device may include the combs, cover plates, or reeds manufactured with anti-microbial materials, such as anti-microbial polymers, coatings, ceramics, copper and its alloys (brasses, bronzes, cupronickel, copper-nickel-zinc, and others), silver, or stainless steel. As such, the hygienic function may be improved for some conditions.

According to a method of practicing the invention using a harmonica with the resistance device attached, the harmonica may be held by the user in either one or both hands by the cover plate(s). According to another embodiment, a supportive device may be used in lieu of hands. The comb or hole(s) may be held up to the user's mouth. The user may then blow and/or draw breath through the comb in a controlled, comfortable manner. The airflow created by the user's lungs across the reeds generates low frequency sound waves. These low frequency sound waves vibrate in the user's respiratory system, resulting in the break-up of mucus and congestion in the user's lungs and sinuses. These effects can be achieved extremely quickly, sometimes in just a few minutes. With regular use, the user is able to breathe clearer, feel better, and experience an improved quality of life. The beneficiaries of improved oxygenation include patients who have decreased lung function and those who are recovering from surgery or trauma, or other acute diseases, long-term wound patients, including diabetics, people whose obesity has restricted their lung function, people with panic attacks and other mood disorders, dementia, chronic fatigue, asthma, and sinus or lung congestion. Meditation is known to have a wide range of beneficial side effects, including a calmer state of mind which is especially important when dealing with the inability to breathe or an impending asthma attack.

According to another aspect of the method, musicians and athletes could use this harmonica with the resistance device to build lung capacity to improve performance. People who meditate could use this device as a meditation aide. People with mild respiratory distress or acute respiratory illness could use this device to help loosen secretions and relax. People interested in improving the oxygenation of their body may use this device to derive the benefits of deep abdominal breathing against variable resistance. By encouraging meditation, the resistance device used with a harmonica can help lower blood pressure and stress hormone levels and the resulting inflammation. The meditative aspect combined with giving people a pleasant activity to do with their hands and mouth could also make this device a smoking cessation or weight loss aide.

According to another embodiment of the invention, the resistance device includes a resistance band which may be removably placed around a harmonica or a pulmonary harmonica to provide further resistance during inspiratory and expiratory muscle training.

According to another embodiment of the invention, the resistance band may include one or more crosshairs for each hole of the central comb of the harmonica. According to such an embodiment, the harmonica will be harder to blow and draw through, which provides increased resistance to help build respiratory strength. This resistance device promotes deep, abdominal breathing, which is continued even after use. The crosshairs in each of the holes also prevent harmonica reeds that might break during use from entering the mouth of the user.

According to another embodiment of the invention, the device is pleasant to use which empowers the patients. In contrast, other non-musical respiratory therapy devices are clearly medical devices that remind the patient of their illness.

According to another embodiment of the invention, the resistance band of the present invention provides significantly more resistance than is found in harmonicas without the crosshairs in the blow/draw holes and improves the harmonica's ability to function as an effective respiratory therapy device.

According to another embodiment of the present invention, the device further includes a plurality of cross-hairs which may prevent a broken reed from entering the player's mouth.

According to another embodiment of the present invention, the device further includes an improved comb which may prevent a broken reed from entering the player's mouth.

According to another embodiment of the present invention, the device includes a central comb for a harmonica with one or more holes for mouthpiece and air movement. According to such an embodiment, crosshairs are provided on a band at each hole, encircling the harmonica which allows a reduced amount of air through the holes, relative a harmonica without the band attached. These crosshairs increase resistance and decrease the chance that broken reed bits will make their way through the holes and into the user's mouth.

According to another embodiment of the present invention, the device includes a central comb for a harmonica with one or more holes for mouthpiece and air movement. According to such an embodiment, rather than the band described in the above paragraph, the invention includes a comb insert with crosshairs in each of the holes to increase resistance and prevent broken reeds from entering the mouth.

According to another embodiment of the present invention, the device includes a central comb for a harmonica with one or more holes for mouthpiece and air movement. According to such an embodiment, a resistance pattern other than crosshairs may be utilized. Such resistance pattern may take on any number of shapes as long as it allows some air to pass through (increasing the resistance) and provides passages of sufficiently narrow size to prevent the passage of broken reed chips.

According to another embodiment of the invention, the central comb of the harmonica is designed with crosshairs in each hole between the openings of the blow/draw holes and the reeds. The crosshairs and supporting materials can be made of plastic, wood, brass, bronze, or stainless steel, or other materials with sufficient integrity, and can be plated, painted, lacquered, shellacked, oiled, anodized, or left as the natural material used to create the crosshairs or functionally similar obstructions and attachment supports.

Accordingly, the device of the present invention device is used by blowing or drawing air through one or more holes along the mouthpiece portion of the comb. Behind the holes are chambers containing at least one reed. The reed is a flat elongated spring typically made of brass, bronze, or stainless steel, which is secured at one end over a slot that serves as an airway. When the free end is made to vibrate by blowing or drawing air through the airway by the reed, the reed blocks and unblocks the airway to produce sound and a resistance that varies with pitch and profiling of the reed. By having a crosshair in each hole of the central comb, the harmonica will be harder to blow and draw through, due to the added resistance, and help build strength in respiratory muscles in the chest and the diaphragm. Although the new device does not need smooth edges, the optimal representation has smooth edges to avoid damaging fragile skin.

According to another embodiment of the invention, the device is manufactured with anti-microbial materials. Accordingly, the hygienic function might be improved for some conditions.

According to another embodiment of the invention, the resistance band is attachable to an existing harmonica or a pulmonary harmonica.

According to another embodiment of the invention, the resistance band is premanufactured as part of the comb of a harmonica.

According to another aspect of the invention, musicians and athletes could use this device to build lung capacity to improve performance without fear of inhaling a broken reed. People interested in improving the oxygenation of their body may use this device to derive the benefits of deep abdominal breathing against gentle resistance, again without fear of inhaling a broken reed.

BRIEF DESCRIPTION OF THE DRAWING FIGURES

The present invention is best understood when the following detailed description of the invention is read in view of the accompanying drawings.

FIG. 18A is a left side view of an embodiment of the resistance band;

FIG. 18B is a front view of an embodiment of the resistance band; FIG. 18C is a top view of an embodiment of the resistance band;

FIG. 18D is a rear view of an embodiment of the resistance band; and

FIG. 18E is a right side view of an embodiment of the resistance band.

DETAILED DESCRIPTION

Figure 1:
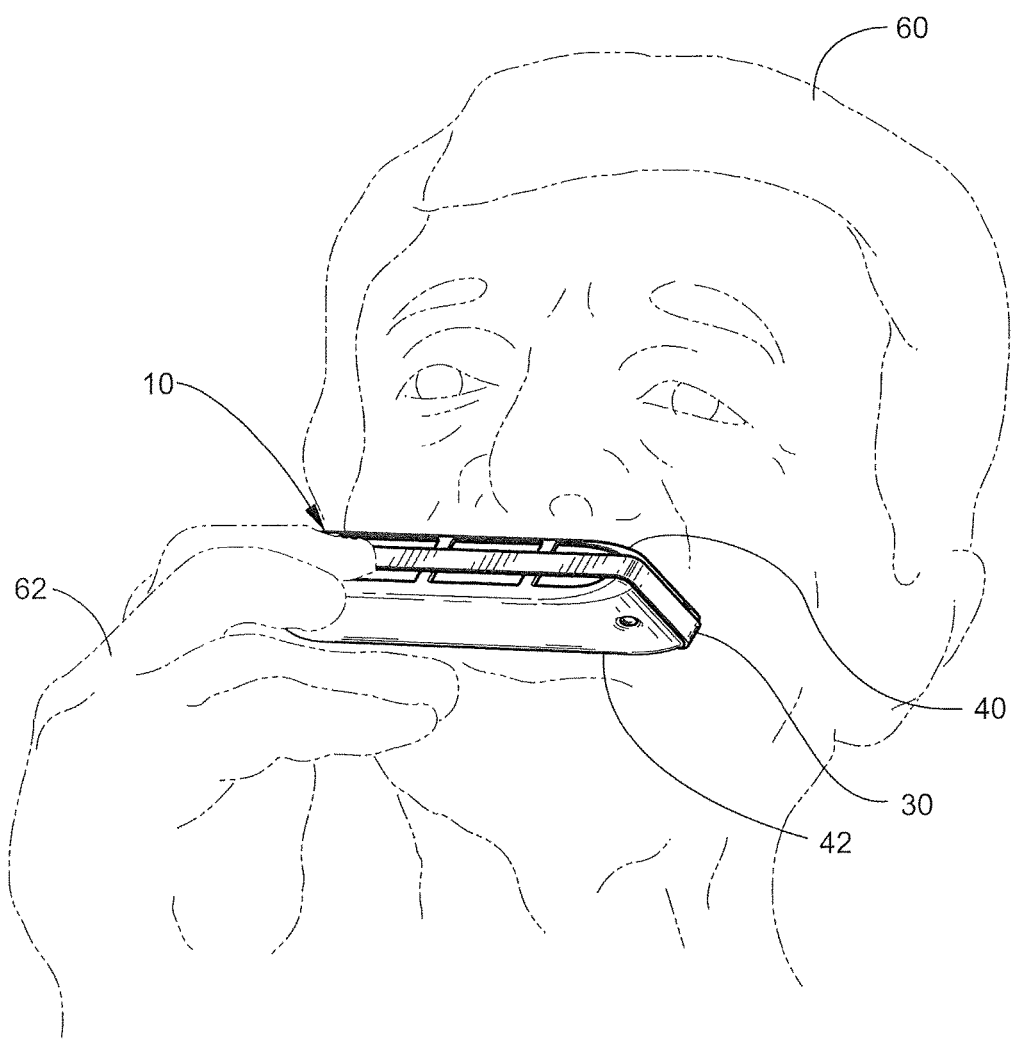
FIG. 1 is an environmental perspective view of an embodiment of the pulmonary harmonica device with the device tipped upwards to make playing single notes easier.
Figure 2:
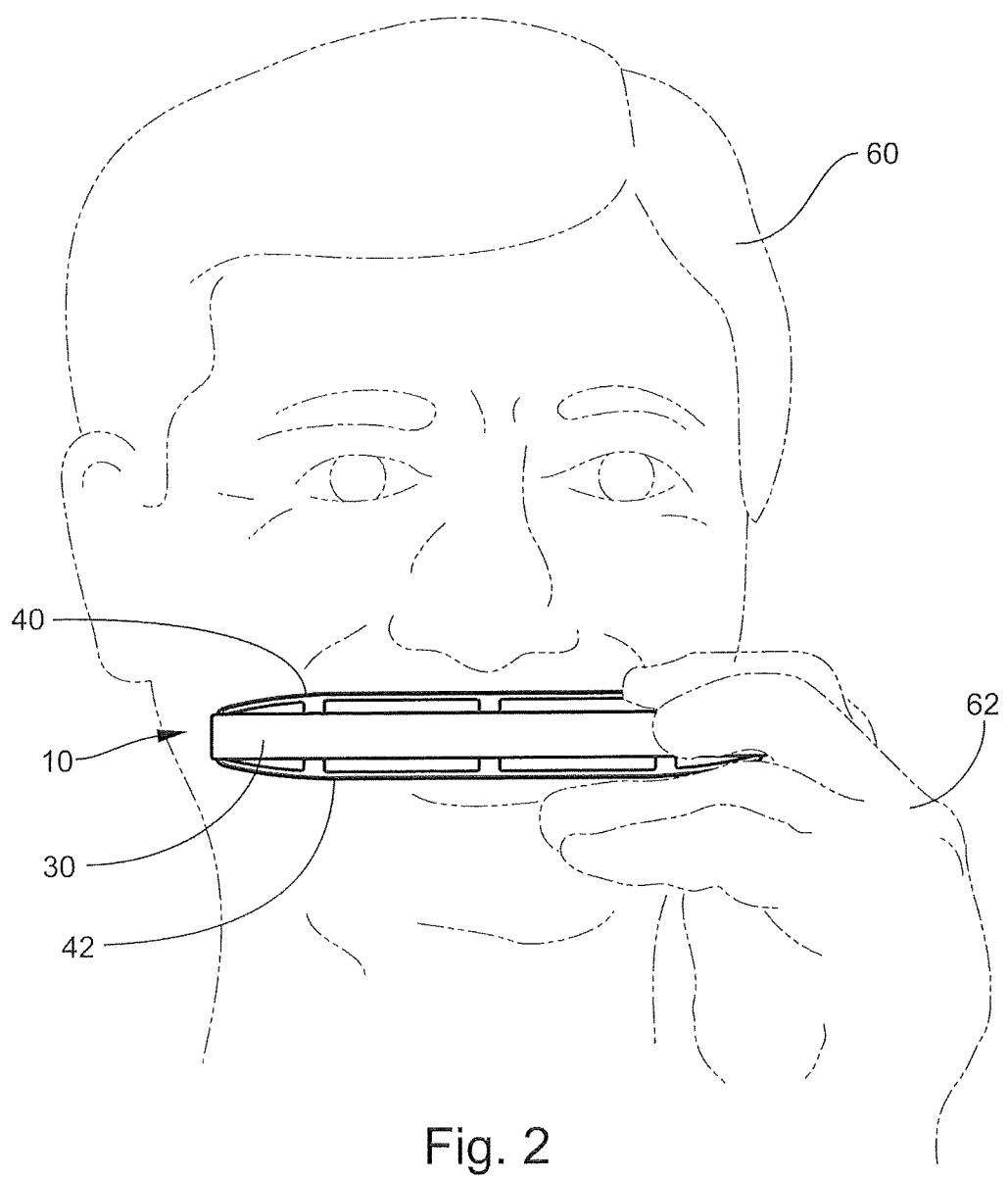
FIG. 2 is an environmental perspective view of an embodiment of the pulmonary harmonica device with the device held straight-in to promote deep abdominal breathing consistent with the method of the present invention.
Figure 3:
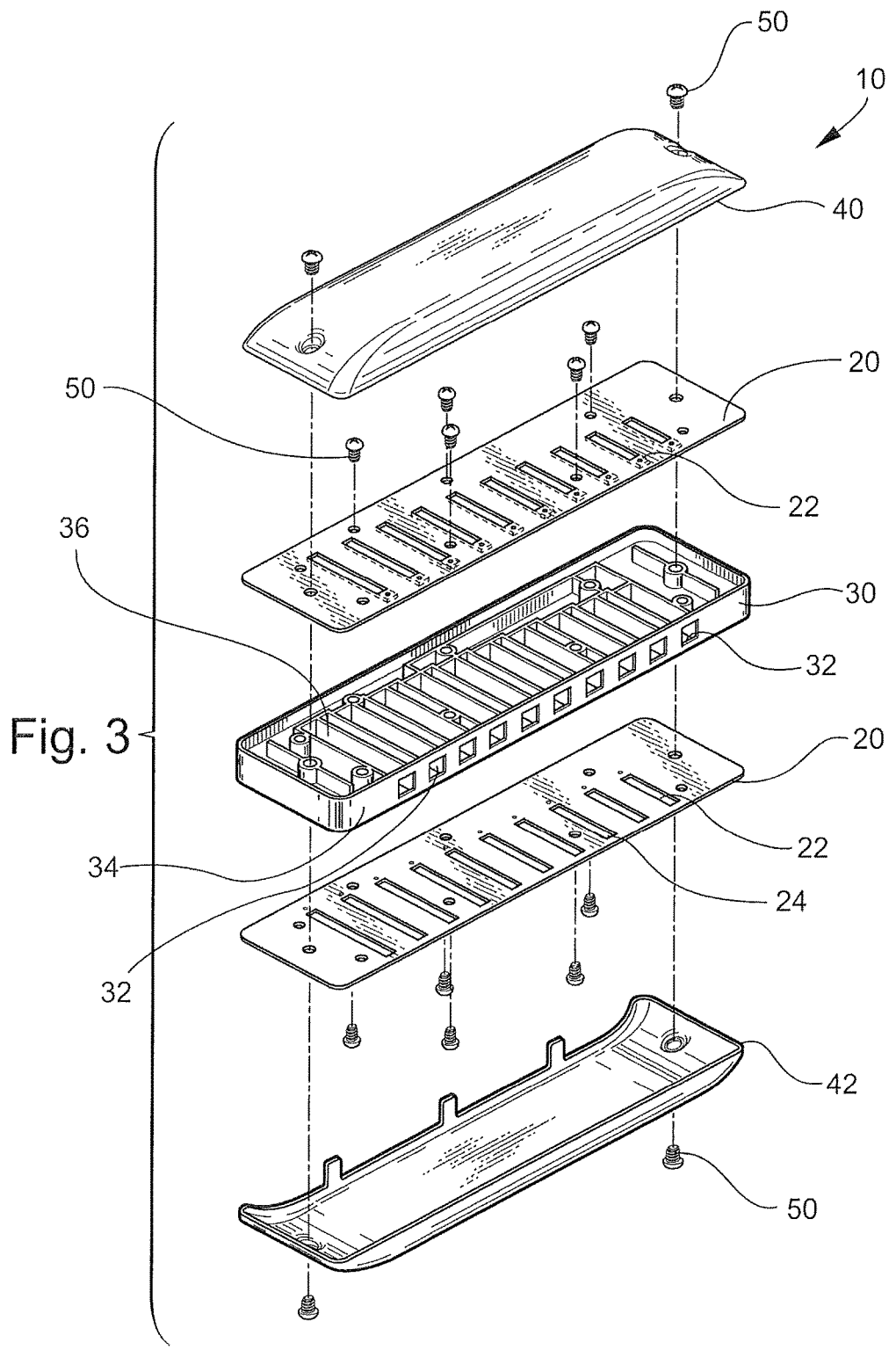
FIG. 3 is an exploded perspective view of an embodiment of the pulmonary harmonica device having ten holes and twenty reeds.
Figure 4:
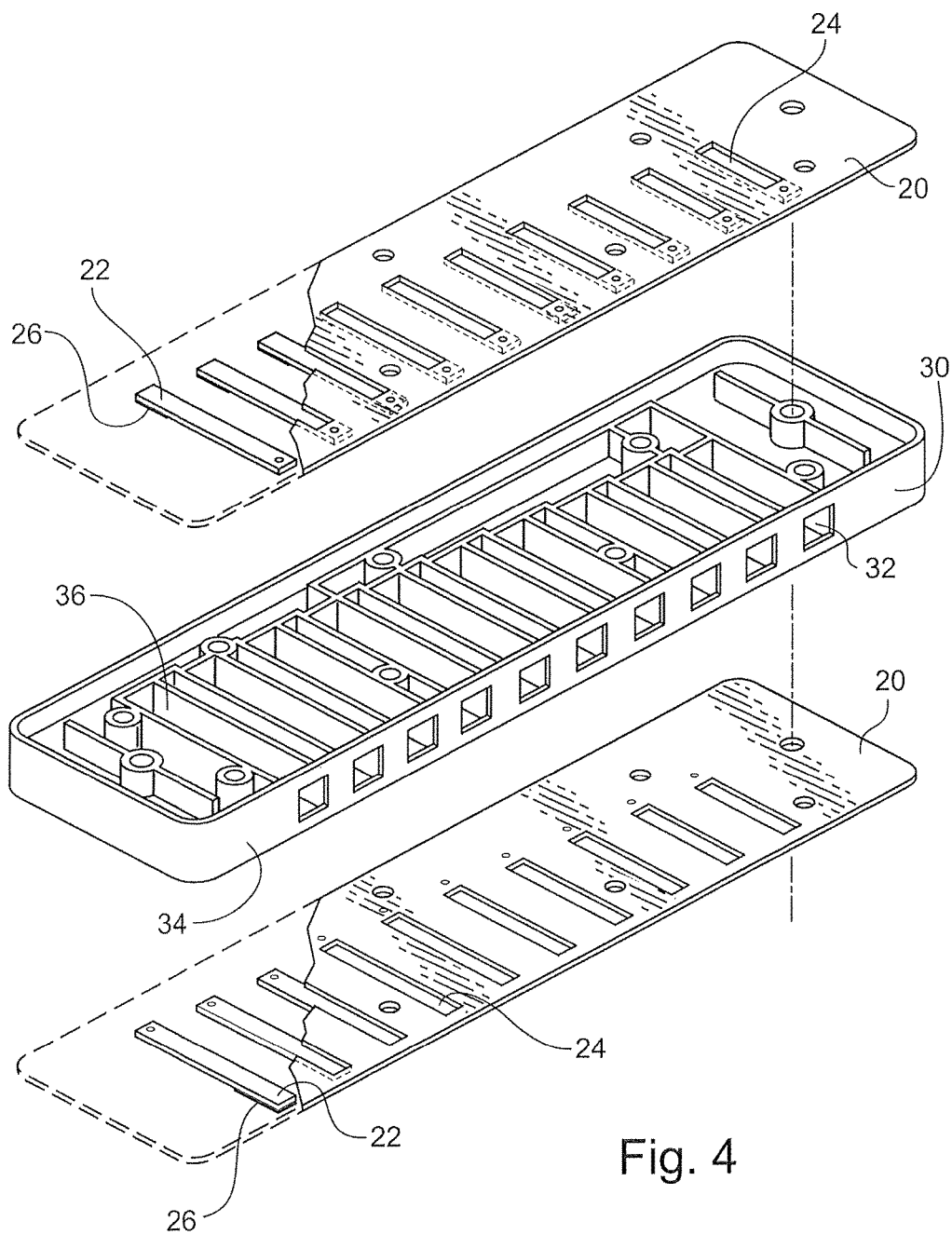
FIG. 4 is a partial exploded perspective view of an embodiment of the pulmonary harmonica device highlighting the reed structure.
Figure 5:
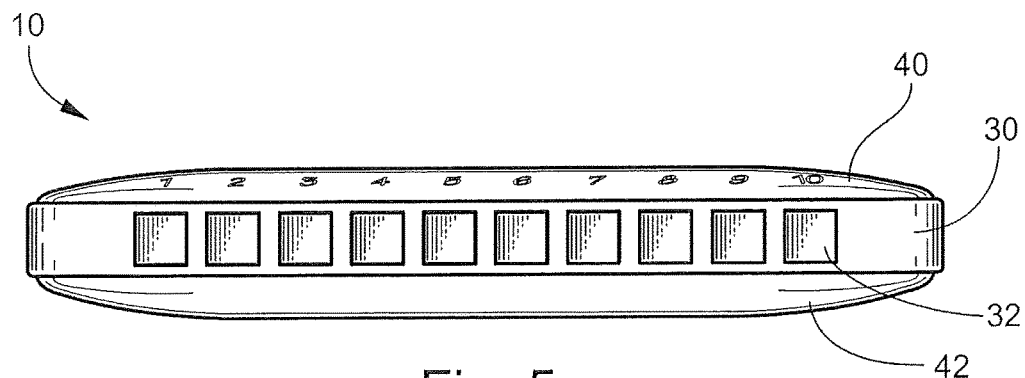
FIG. 5 is a side view of an embodiment of the pulmonary harmonica device.
Figure 6:
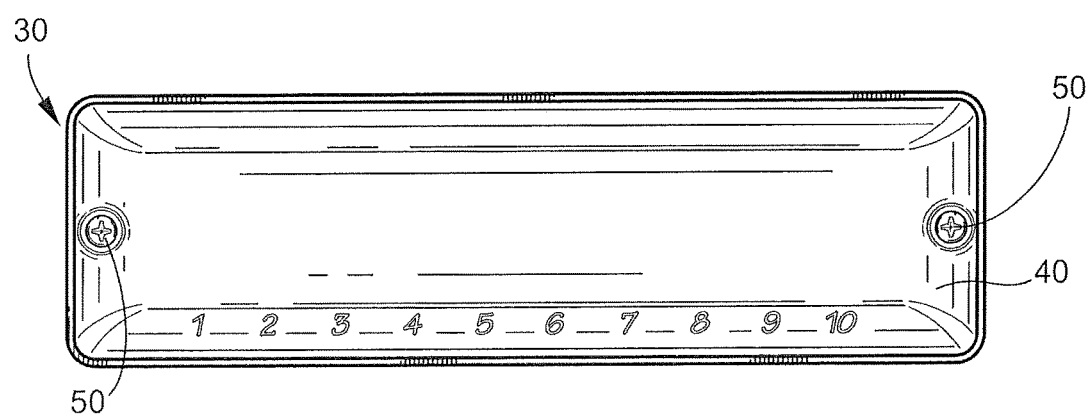
FIG. 6 is a top view of an embodiment of the pulmonary harmonica device.
Figure 7:
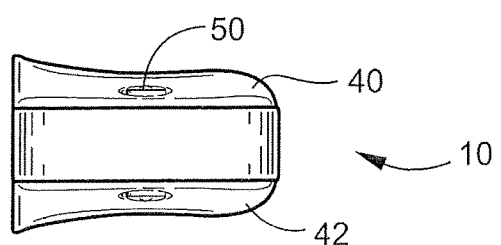
FIG. 7 is a an end view of an embodiment of the pulmonary harmonica device.

Referring now, specifically to the drawings, a pulmonary harmonica is shown generally at reference numeral 10. As shown in FIGS. 1 and 2, the harmonica 10 and method, which is especially shown in FIG. 2, of the present invention can be used by anyone, just about anywhere, without musical talent or experience with musical instruments, and with no prior knowledge or experience with meditation or controlled breathing exercises and techniques. As shown in FIGS. 3 and 4, the parts of the pulmonary harmonica 10 include a comb 30 or other structure to hold the reeds 22 in place, two or more reeds 22, one or more reed plates 20 or other structure to allow for a gap through which the reed 22 passes in use, a housing in the form of one or more cover plates 40, 42, fastening hardware 50, and low frequency sound waves. The reed plate 20 is defined as a structure to allow for a gap through which the reed 22 passes in use. The reeds 22 may have weights 26 attached the ends of the reeds 22.

The cover plates 40, 42 and comb 30 can be made of plastic, wood, brass, aluminum, bronze, or stainless steel, or other materials with sufficient integrity (with or without antimicrobial properties), and can be plated, painted, lacquered, shellacked, oiled, or anodized. The reeds 22 and reed plates 20 can be made of brass, bronze, German silver, stainless steel, aluminum, plastic, titanium, or other material with appropriate spring-like characteristics. Alternatively, it may be molded out of a single piece of plastic, ceramic, or like materials. The tuning of the reeds 22 can be in any key with two restrictions: low-pulse generating methodology is followed (i.e., reeds tuned to resonant frequencies, such as the notes that form a major or minor chord), and the pulses generated are sufficiently low to be felt in the upper chest. Although people's sensitivities to chest pulsing varies, harmonicas meeting the criteria for this invention and pragmatically low enough in frequency to be effective will need to have their lowest tuned reed of the reeds 22 no higher than 150 Hz.

Figure 8:
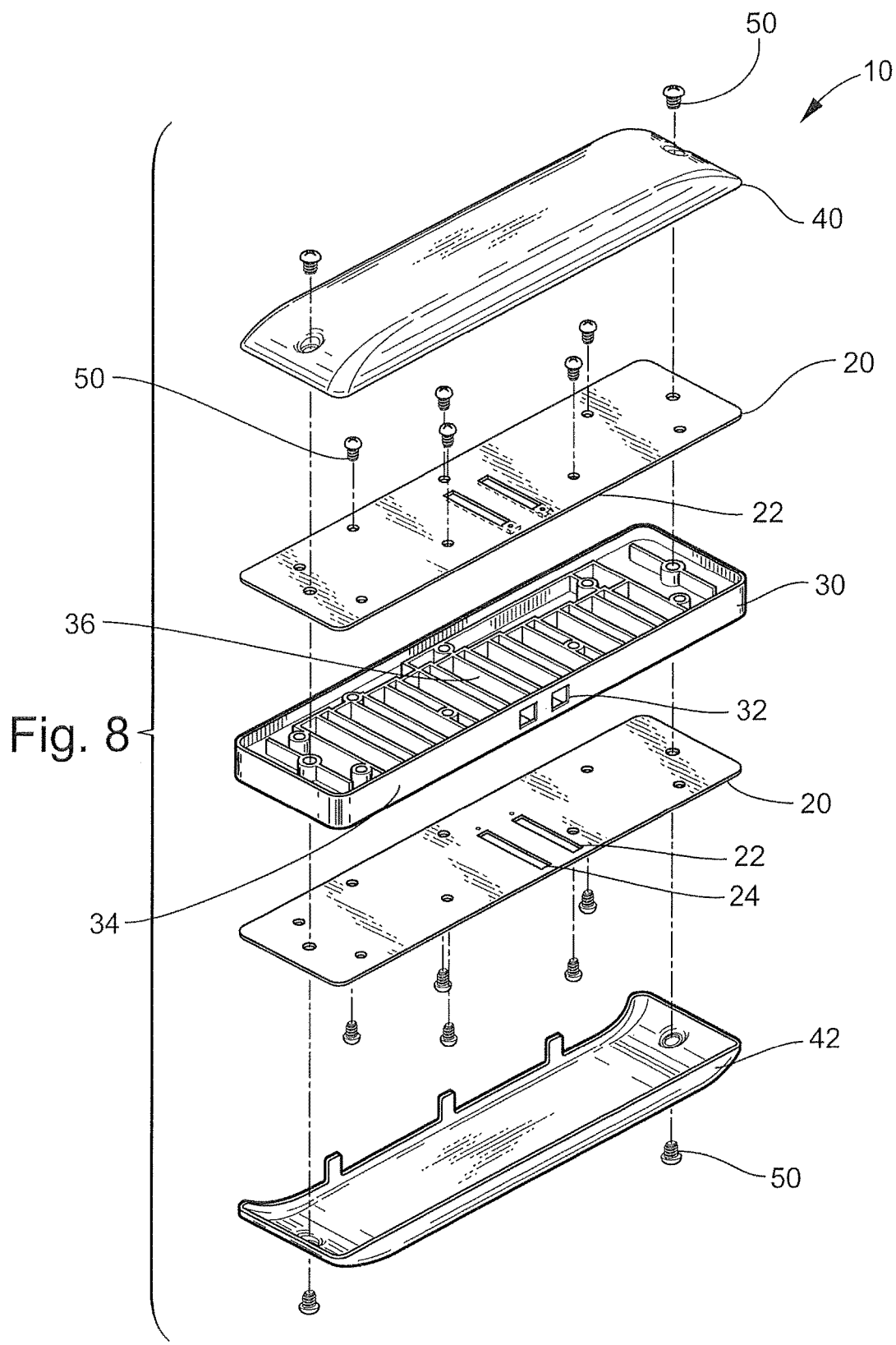
FIG. 8 is an exploded perspective view of an embodiment of the pulmonary harmonica device having two holes and four reeds.
Figure 9:
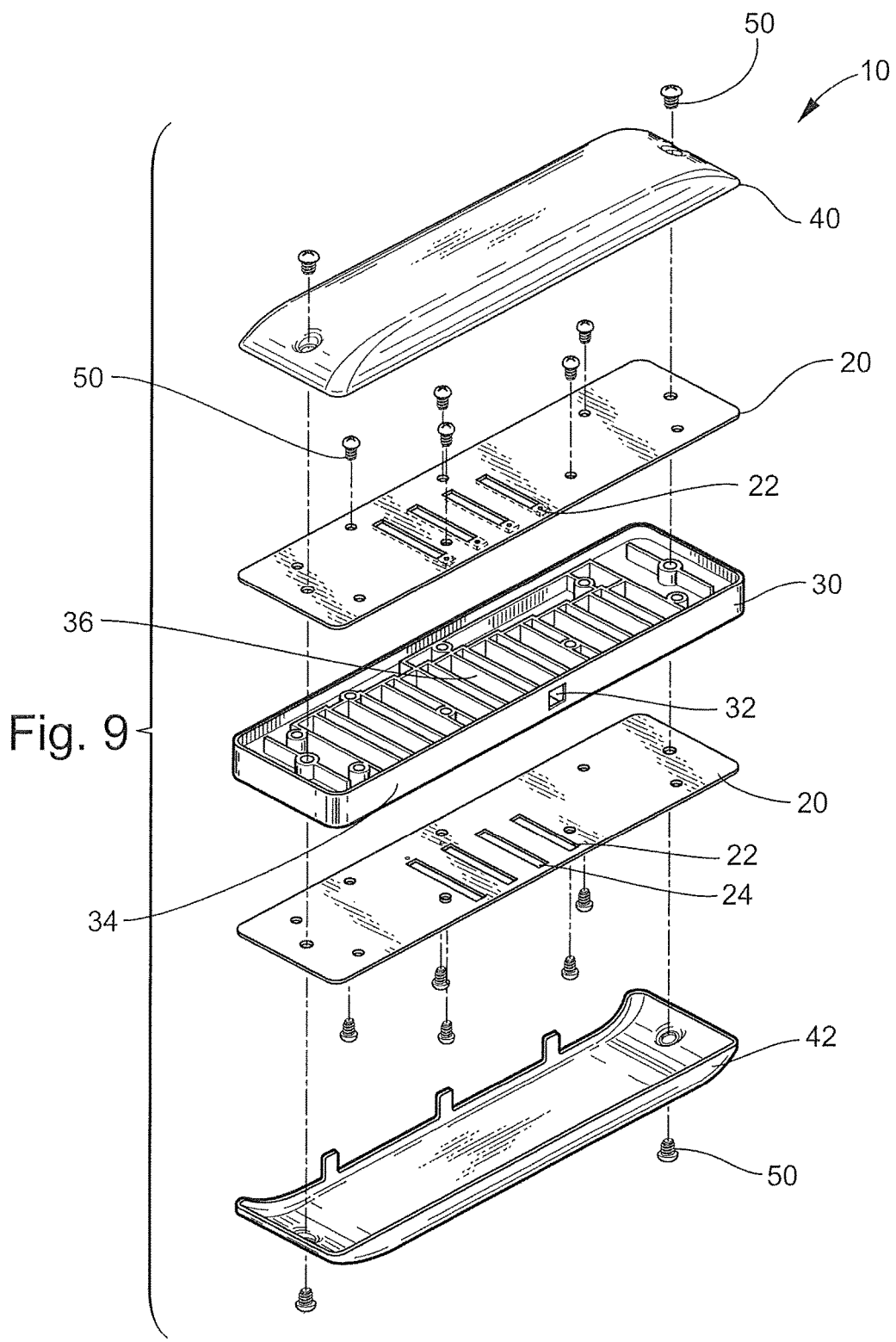
FIG. 9 is an exploded perspective view of an embodiment of the pulmonary harmonica device having one hole and four reeds.
Figure 10:
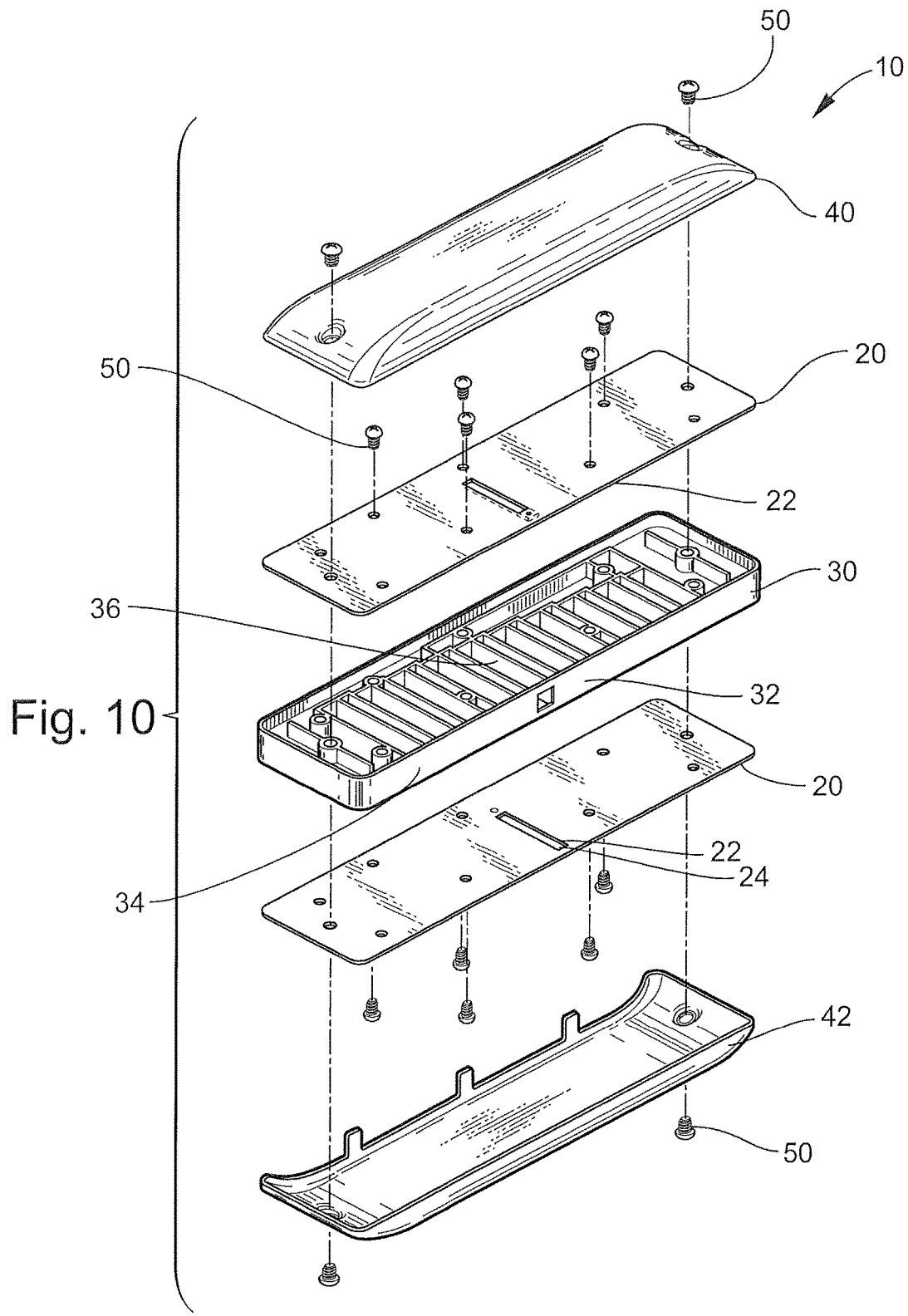
FIG. 10 is an exploded perspective view of an embodiment of the pulmonary harmonica device having one hole and two reeds.
Figure 11:
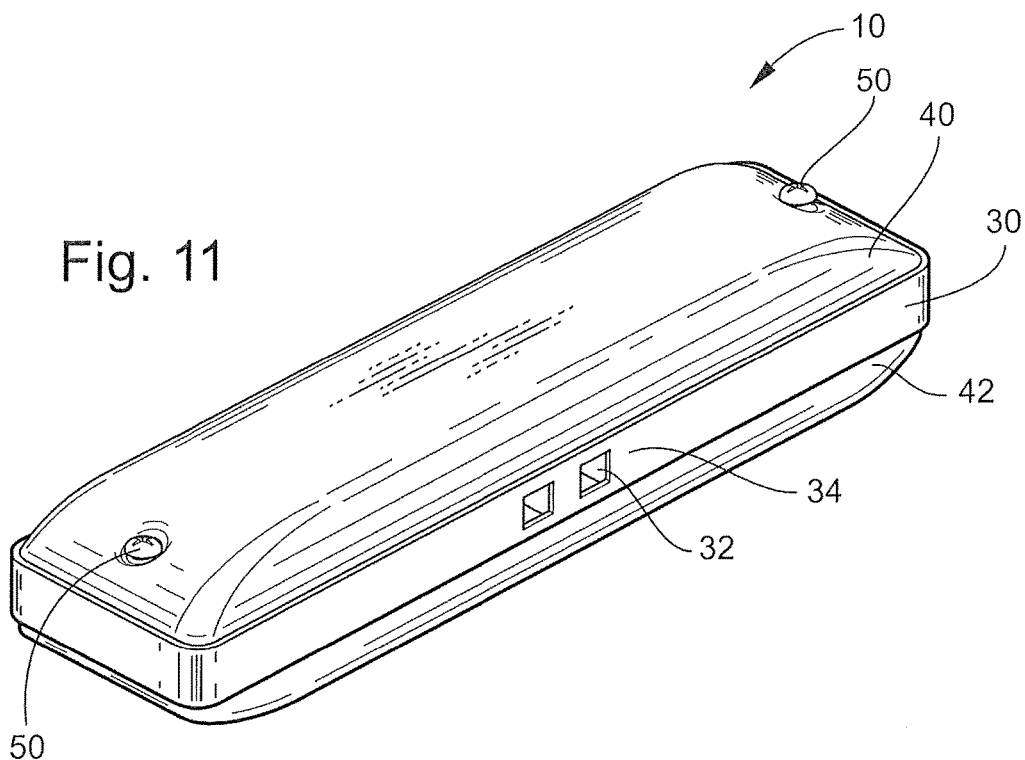
FIG. 11 is a perspective view of an embodiment of the pulmonary harmonica device having two holes.
Figure 12:
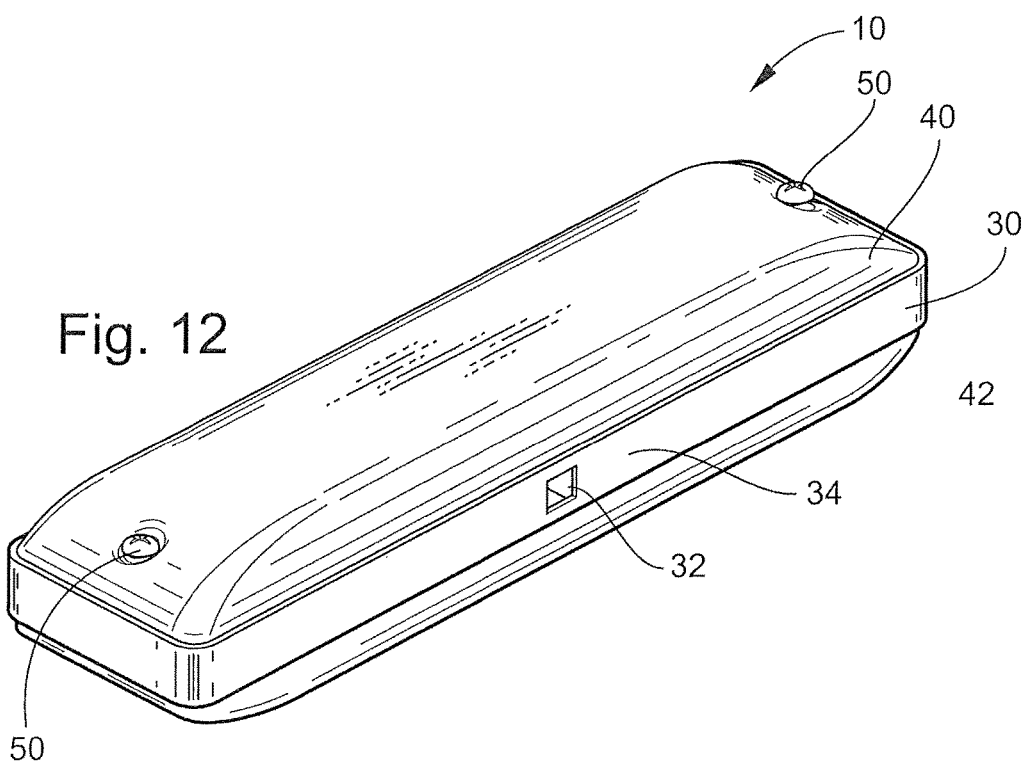
FIG. 12 is a perspective view of an embodiment of the pulmonary harmonica device having one hole.

The harmonica 10 is used by blowing or drawing air through one or more holes 32 along the mouthpiece portion 34 of the comb 30. Behind the holes are chambers 36 containing at least one reed 22 which may be attached to a reed plate 20. The reed 22 is a flat elongated spring typically made of brass, bronze, or stainless steel, which is secured at one end over a slot 24 that serves as an airway. When the free end of the reed 22 is made to vibrate by blowing or drawing breath across it, it blocks and unblocks the airway to produce sound and a resistance that varies with pitch. By tuning the reeds 22 to vibrate at specific low frequencies, a harmonic resonance is set up, which pulses the lungs of a user 60 and helps loosen secretions and enable expectoration. Low-tuned reeds 22 are heavy and hard to blow and draw relative to a traditional harmonica. For instance, for a traditional or "standard" harmonica, with metal reeds, the key of C set of reeds is about 2.22 grams. In contrast, the metal reed set of the pulmonary harmonica 10 of the present invention weighs 2.66 grams. These low-tuned reeds 22 provide a resistance that helps build respiratory strength. By having some reeds 22 tuned higher and others lower, variable resistance training can be accomplished. By having the reeds 22 tuned to full diatonic scales of chords in its major or minor key, dissonant notes and chords are eliminated and the improved pulmonary harmonica 10 can be used by anyone regardless of musical background or ability. Ten-hole tuning as shown in FIG. 3, can allow two octaves of the complete diatonic scale of chords, and includes spiral tuning that can be used for a wide variety of songs. Fewer than 10 holes, as in FIGS. 8 12, can also be used with this spiral tuning and a full octave can still be achieved. By having smooth edges on all surfaces of the device 10 and only pleasant sounds, the device is safe and encourages compliance. Because the device 10 makes noise, it is easy to monitor compliance by a user 60. The draw and blow notes can also be tuned to as few as one extended chord so that people using the device 10 in a group can all sound harmonious when using the device together and with no knowledge of music or what to play.

The harmonica 10 is intended for use by people 60 with respiratory disorders or who seek the benefits of improved oxygenation and meditative relaxation. As shown in FIG. 1 and FIG. 2, the harmonica 10 is held by the user 60 in either one or both hands 62 by the cover plate(s) 40, 42 or by a holder designed for the purpose. The comb 30 and/or blow/draw hole(s) 32 is held up to the user's 60 mouth. The user 60 then blows and/or draws breath through comb 30 in a controlled, comfortable manner. Preferably, the harmonica 10 is utilized as in FIG. 2 with the device 10 held straight-in relative to the mouth of the user 60 to promote deep abdominal breathing. The airflow created by the user's 60 lungs across the reeds 22 generates low frequency sound waves. These low frequency sound waves vibrate in the user's 60 respiratory system resulting in the break-up of mucus and congestion in the user's 60 lungs and sinuses. The harmonica 10 contemplates a regimen of controlled breathing using the device. These effects can be achieved extremely quickly. With regular use of the harmonica 10, the user 60 is able to breathe clearer, feel better, and experience an improved quality of life.

Referring now specifically to FIGS. 13, 14, 15, 16, 17A, 17B, 18A, 18B, 18C, 18D, and 18E, the invention is a resistance device for a harmonica such as pulmonary harmonica and further comprises a resistance band 100 which may be applied to a harmonica such as a pulmonary harmonica 10. According to one embodiment of the invention, the resistance band 100 is applied around the exterior of the harmonica 10 in a way which increases the resistance to air flow whether the air is blown or drawn from the harmonica 10. In an alternate embodiment (not shown), rather than applied to exterior of the harmonica, the resistance band may be built into the comb 30.

Figure 13:
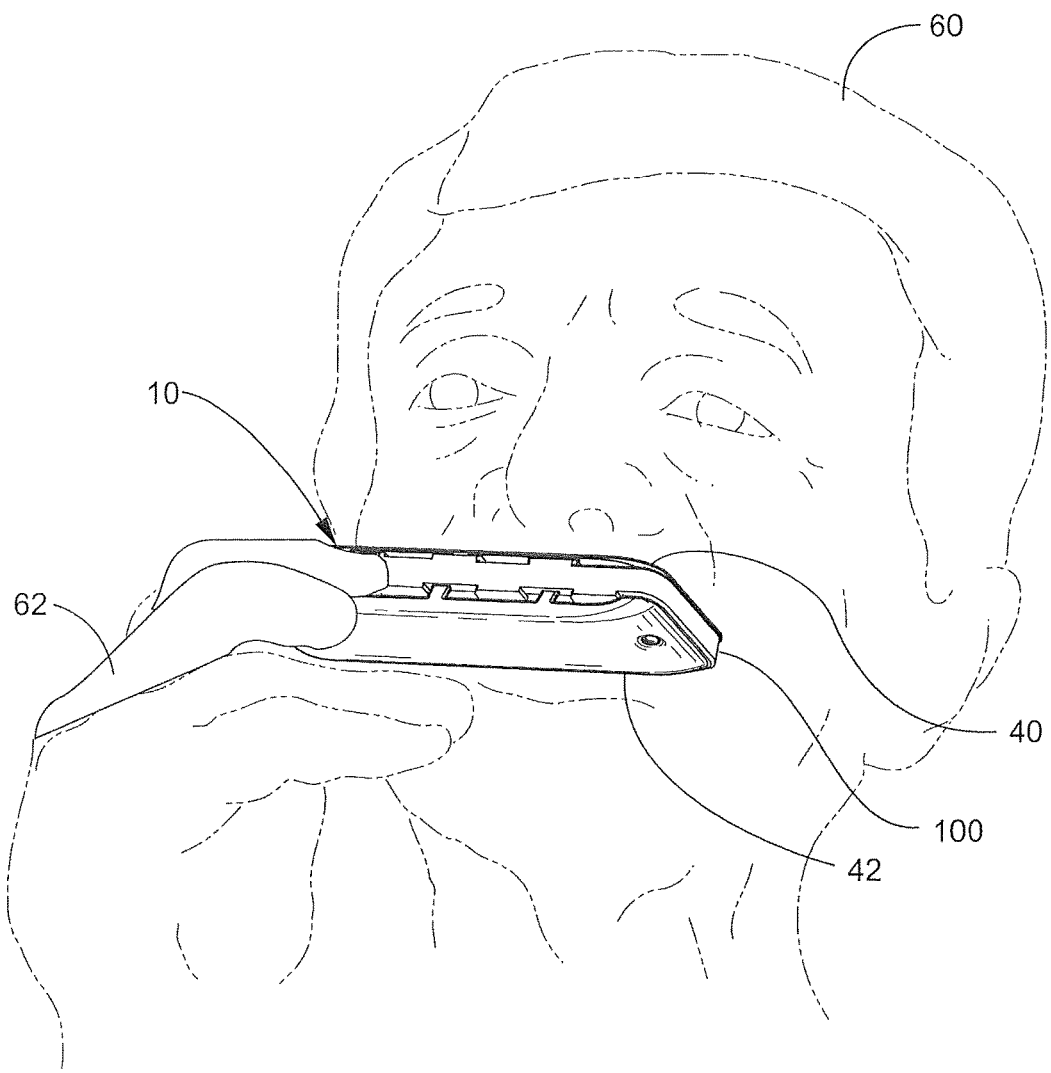
FIG. 13 is an environmental perspective view of an embodiment of the resistance band attached to a pulmonary harmonica device with the device tipped upwards to make playing single notes easier.
Figure 14:
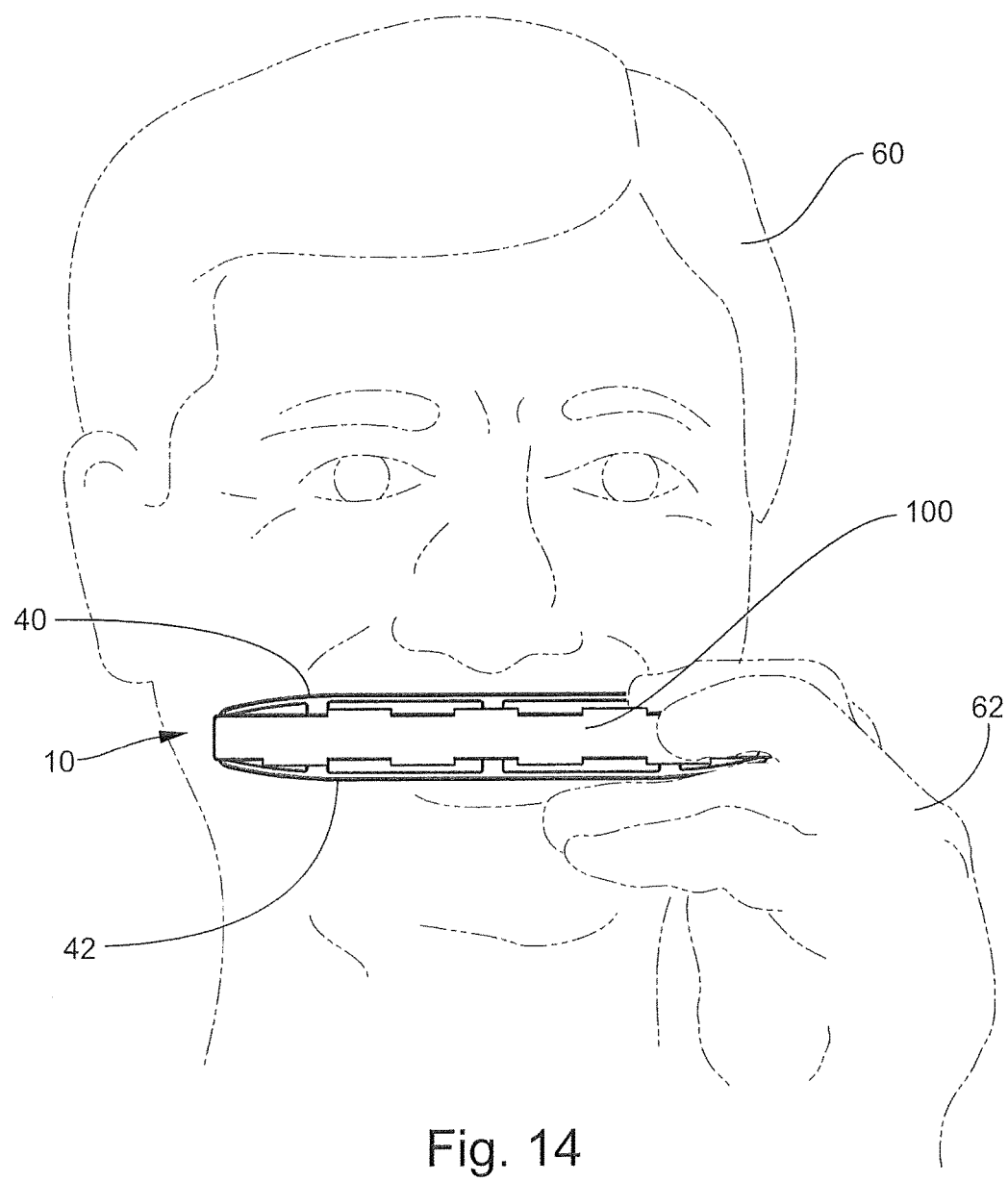
FIG. 14 is an environmental perspective view of an embodiment of the resistance band attached to a pulmonary harmonica device with the device held straight-in to promote deep abdominal breathing consistent with the method of the present invention.
Figure 15:
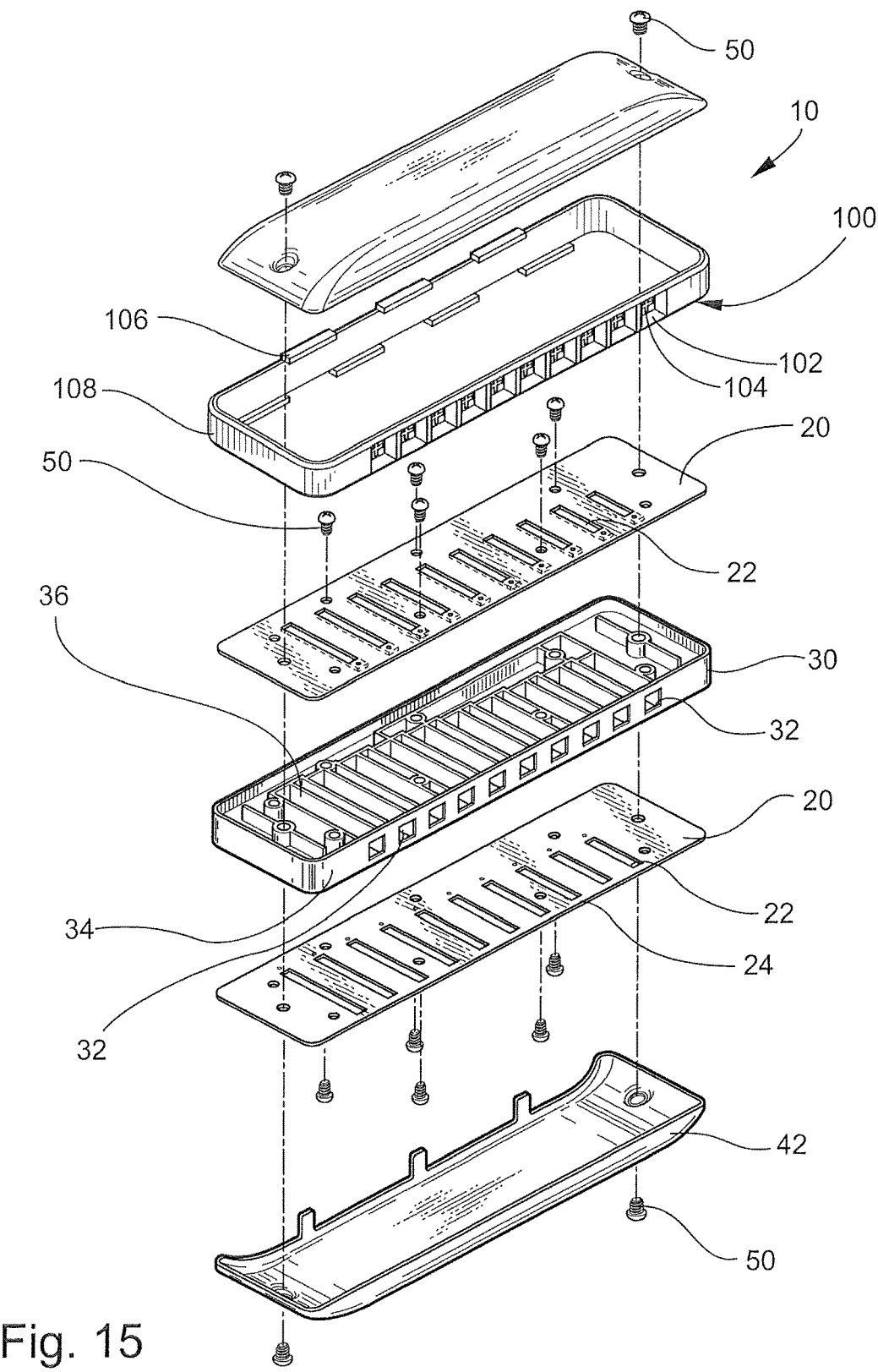
FIG. 15 is an exploded view perspective view of an embodiment of the resistance band and pulmonary harmonica device.

As shown in FIGS. 13 and 14, the resistance band 100 may be applied around the exterior of the harmonica 10. As shown in FIG. 13, the user may tip the device upwards thereby making playing single notes easier. Alternatively, as shown in FIG. 14 the user may hold the device straight-in to promote deep abdominal breathing consistent with the method of the present invention.

As shown in FIGS. 15, 16, 17A, 17B, 18A, 18B, 18C 18D, and 18E, a pulmonary harmonica 10 may be assembled with the resistance band 100 applied around the comb 30. As discussed above, an alternate embodiment (not shown) includes the resistance band 100 built into the comb 30 itself. The resistance band 100 includes a band portion 108 which encircles the comb 30. The resistance band includes a plurality of attachment points 106 which hold the resistance band 100 to the comb 30. As shown, the attachment points 106 may be in the form of perpendicular tabs disposed at a top and bottom portion of a rear portion of the band. The attachment points 106 may wrap around the comb 30 on a side opposite the side where the holes 32 are located.

The resistance band 100 also includes one or more indentions 102 which are sized to fit within the holes of the comb 30 when the band is wrapped around the comb 30. The indentations 102 are located on a side opposite from the attachment points 106. The indentations 102 serve at least two purposes. One purpose is to hold the resistance band 100 to the comb 30 and to the harmonica 10. Another purpose of the indentations 102 is to further narrow the size of the hole 32 opening to thereby increase the resistance to air flow through the hole 32, whether through blow or draw. Preferably, the number of indentations 102 is equal to the number of holes 32 of the comb 30.

Figure 16:
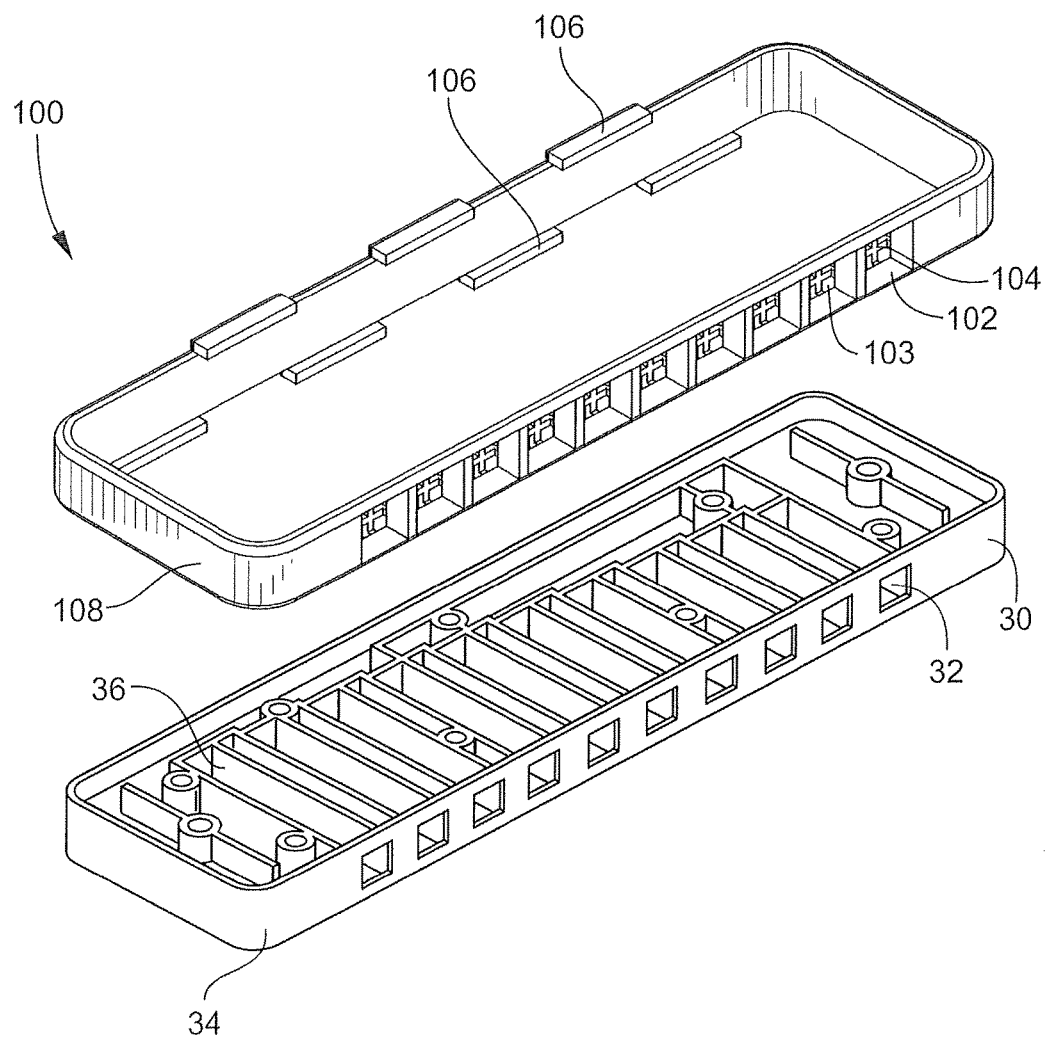
FIG. 16 is a perspective view of an embodiment of the resistance band in exploded view above a comb of a pulmonary harmonica device.
Figure 17A:
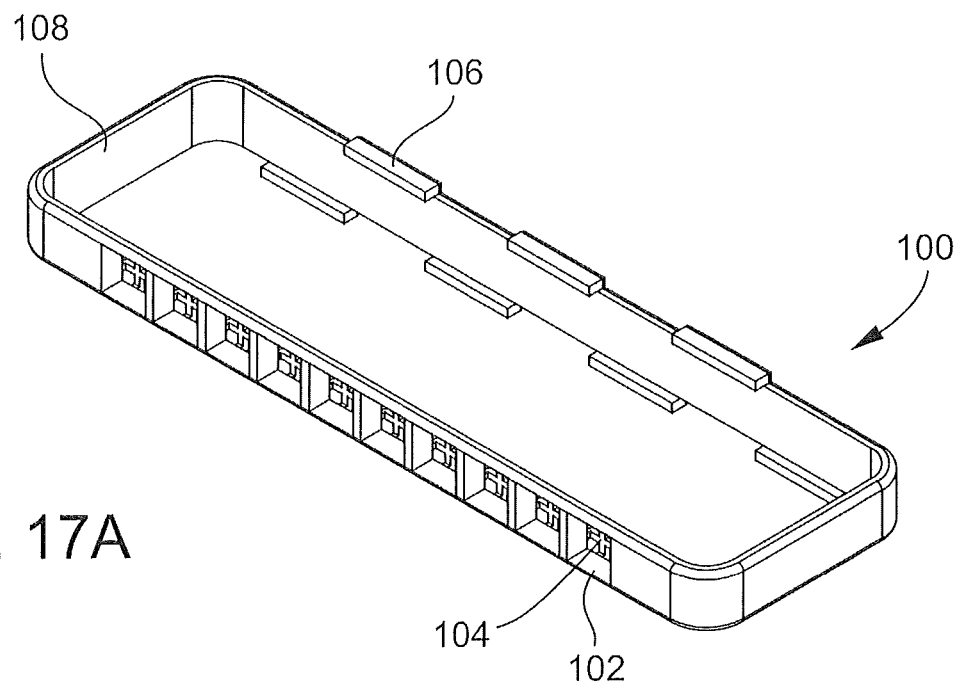
FIG. 17A is a front perspective view of an embodiment of the resistance band.
Figure 17B:
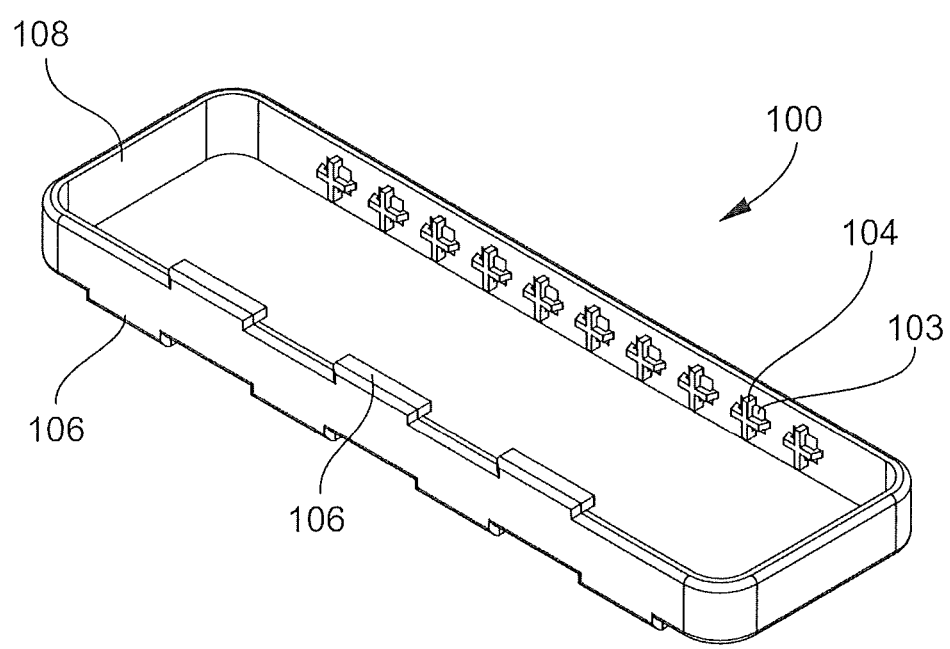
FIG. 17B is a rear perspective view of an embodiment of the resistance band.

Each indentation 102 of the resistance band 100 further includes a crosshair 104. As shown, the crosshair 104 includes a pair of intersecting perpendicular bars defining four air voids 103. The crosshairs 104 may include other shapes and patterns not shown in the drawings. Further, the crosshairs 104 may include more than two bars defining more than four air voids 103 or as few two or three air voids 103. As shown in FIG. 17B, the crosshairs 104 extend inward from the band portion 108. That is, they extend into the holes 32 of the comb as shown in FIG. 16. The air voids 103 allow air to pass through to the holes 32 of the comb 30. Because the size and orientation of the crosshairs 104 defines the size of the air voids 103, the size and orientation of the crosshairs 104 will also define the amount of air and, hence, resistance, to air flow, allowed into and out of the holes 32 of the comb 30. In this way, the resistance band 100 increases resistance of air flow through the holes 32 of the comb 30 in a way which furthers the purpose of the pulmonary harmonica. Additionally, in the event that one or more of the reeds 22 breaks or becomes dislodged from reed plate 20, the crosshairs 104 may prevent the reeds or the pieces of the reeds from exiting through the holes 32 of the comb 32.

A pulmonary harmonica 10, method for using a pulmonary harmonica 10, and a resistance device such as a resistance band 100 according to the invention has been described. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

What is claimed is:

1. A pulmonary harmonica device for promoting deep abdominal breathing by a user and for producing a sound comprising:
   an outer housing;
   a comb having a mouthpiece portion and one or more holes;
   one or more reed plates;
   a plurality of reeds, located on the reed plates;
   fastening hardware for securing the reeds, the reed plates, the comb, and the cover plates together; and
   a breathing resistance device having at least one resistance pattern fitting inside each of the one or more holes of the comb for providing resistance to air flow through the holes.

2. The pulmonary harmonica device of claim 1 wherein the breathing resistance device further comprises: a band; an attachment point; and at least one indentation fitting inside a hole of a comb of a harmonica, and wherein the resistance pattern consists of crosshairs.

3. The pulmonary harmonica device of claim 2 wherein the band wraps around the comb.

4. The pulmonary harmonica device of claim 3 wherein the attachment point comprises perpendicular tabs disposed at a top and bottom portion of a rear portion of the band for firmly holding band to the comb.

5. The Pulmonary harmonica device of claim 1 wherein each one of the plurality of reeds provides a resistance that helps build respiratory strength.

6. The pulmonary harmonica device of claim 1 wherein a lowest tuned reed of the plurality of reeds is no higher than 150 Hz.

7. The pulmonary harmonica device of claim 1 wherein fastening hardware is selected from the group comprising screws, bolts, nails, welds, rivets, melds, and glues.

8. The pulmonary harmonica device of claim 1 wherein at least one reed is tuned to 136.1 Hz.

9. The pulmonary harmonica device of claim 1 wherein the reeds are heavier than a set of reeds associated with a "standard" harmonica.

10. The pulmonary harmonica device of claim 1 wherein the plurality of reeds collectively weigh 2.66 grams.

11. The pulmonary harmonica of claim 1 wherein the resistance pattern is plastic.

12. The pulmonary harmonica of claim 1 wherein the resistance pattern is made from a material selected from a group consisting of: plastic, wood, brass, bronze, and steel.

13. The pulmonary harmonica of claim 12 wherein the material of the resistance pattern has a finish applied wherein the finish is selected from the group consisting of: plating, painting, lacquering, shellacking, oiling, and anodizing.

14. The pulmonary harmonica of claim 1 wherein the resistance pattern is fixed.

15. The pulmonary harmonica of claim 1 wherein the resistance pattern is removable.

* * * * *